(12) United States Patent
Wollowick et al.

(10) Patent No.: US 10,959,782 B2
(45) Date of Patent: Mar. 30, 2021

(54) SYSTEMS AND METHODS FOR INTRA-OPERATIVE IMAGE ACQUISITION AND CALIBRATION

(71) Applicant: Depuy Synthes Products, Inc., Raynham, MA (US)

(72) Inventors: Noah D. Wollowick, Westport, CT (US); Andrew Cooper, Largo, FL (US); Cameron Albert, Powhatan, VA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 16/744,167

(22) Filed: Jan. 15, 2020

(65) Prior Publication Data
US 2020/0146753 A1    May 14, 2020

Related U.S. Application Data

(63) Continuation of application No. 16/227,451, filed on Dec. 20, 2018, now Pat. No. 10,610,305, which is a
(Continued)

(51) Int. Cl.
*A61B 34/10* (2016.01)
*G09G 5/36* (2006.01)
(Continued)

(52) U.S. Cl.
CPC ............ *A61B 34/10* (2016.02); *A61B 6/46* (2013.01); *A61B 6/563* (2013.01); *G06T 7/70* (2017.01);
(Continued)

(58) Field of Classification Search
None
See application file for complete search history.

(56) References Cited

U.S. PATENT DOCUMENTS

| 5,715,836 A | 2/1998 | Kliegis et al. |
| 6,205,411 B1 | 3/2001 | DiGioia, III et al. |

(Continued)

FOREIGN PATENT DOCUMENTS

| JP | 2005-130928 | 5/2005 |
| JP | 2009136384 A | 6/2009 |

(Continued)

OTHER PUBLICATIONS

Extended European Search Report for EP 15755633.3 dated Sep. 18, 2017.
(Continued)

*Primary Examiner* — Eileen M Adams
(74) *Attorney, Agent, or Firm* — Venkatesh Krishnamoorthy; Silicon Valley Patent Group, LLP

(57) ABSTRACT

A system and method utilizing a camera device containing an inertial measuring unit or similar orientation mechanism to calibrate alignment of the camera device according to a primary image such as an image displayed on an imaging screen, and then utilizing this calibration data to guide the system or user in acquiring a spatially aligned digital image using the camera device. Steps include recording the spatial orientation of the camera in at least two spatial dimensions when aligned with the primary image and guiding the camera into relative alignment with the imaging screen when taking a picture.

18 Claims, 8 Drawing Sheets

Related U.S. Application Data continuation of application No. 15/601,800, filed on May 22, 2017, now Pat. No. 10,182,871.

(60) Provisional application No. 62/339,926, filed on May 22, 2016.

(51) Int. Cl.
    *G06T 7/80*         (2017.01)
    *G06T 7/70*         (2017.01)
    *A61B 6/00*        (2006.01)
    *G16H 30/20*      (2018.01)
    *A61B 34/20*      (2016.01)

(52) U.S. Cl.
    CPC ............... *G06T 7/80* (2017.01); *G09G 5/363* (2013.01); *G16H 30/20* (2018.01); *A61B 6/487* (2013.01); *A61B 6/505* (2013.01); *A61B 2034/108* (2016.02); *A61B 2034/2048* (2016.02); *G06T 2207/30004* (2013.01); *G06T 2207/30244* (2013.01)

(56) References Cited

U.S. PATENT DOCUMENTS

| | | |
|---|---|---|
| 6,614,453 B1 | 9/2003 | Suri et al. |
| 8,249,318 B2 | 8/2012 | Schmitt et al. |
| 8,311,791 B1 | 11/2012 | Avisar |
| 8,484,001 B2 | 7/2013 | Glozman et al. |
| 8,635,082 B2 | 1/2014 | Woods et al. |
| 8,831,324 B2 | 9/2014 | Penenberg |
| 8,917,290 B2 | 12/2014 | Beck |
| 10,182,871 B2 | 1/2019 | Wollowick et al. |
| 2004/0171924 A1 | 9/2004 | Mire et al. |
| 2005/0015005 A1 | 1/2005 | Kockro |
| 2007/0015999 A1 | 1/2007 | Heldreth et al. |
| 2007/0066917 A1 | 3/2007 | Hodorek et al. |
| 2007/0078678 A1 | 4/2007 | Disilvestro et al. |
| 2008/0021299 A1 | 1/2008 | Meulink |
| 2008/0075348 A1 | 3/2008 | Rappaport et al. |
| 2008/0120262 A1 | 5/2008 | Habets et al. |
| 2008/0161680 A1 | 7/2008 | von Jako et al. |
| 2009/0089034 A1 | 4/2009 | Penney et al. |
| 2010/0249507 A1 | 9/2010 | Prisco et al. |
| 2010/0250571 A1 | 9/2010 | Pierce et al. |
| 2010/0256479 A1 | 10/2010 | Park et al. |
| 2011/0082367 A1 | 4/2011 | Regazzoni |
| 2011/0268325 A1 | 11/2011 | Teichman et al. |
| 2011/0313424 A1 | 12/2011 | Bono et al. |
| 2011/0319941 A1 | 12/2011 | Bar et al. |
| 2012/0016269 A1 | 1/2012 | Moctezuma de la Barrera |
| 2012/0157887 A1 | 6/2012 | Fanson et al. |
| 2012/0194505 A1 | 8/2012 | Beck |
| 2012/0194666 A1 | 8/2012 | Jackson |
| 2013/0060146 A1 | 3/2013 | Yang et al. |
| 2013/0072821 A1 | 3/2013 | Odermatt et al. |
| 2013/0135721 A1 | 5/2013 | An et al. |
| 2013/0197687 A1 | 8/2013 | Pavlovskaia et al. |
| 2013/0296078 A1* | 11/2013 | Solheim ................. A63B 60/42 473/409 |
| 2014/0003700 A1 | 1/2014 | Hermosillo Valadez et al. |
| 2014/0062863 A1 | 3/2014 | Yu et al. |
| 2014/0073907 A1 | 3/2014 | Kumar et al. |
| 2014/0303938 A1 | 10/2014 | Schoenefeld et al. |
| 2014/0378828 A1 | 12/2014 | Penenberg et al. |
| 2015/0150523 A1 | 6/2015 | Sirpad et al. |
| 2016/0100909 A1 | 4/2016 | Wollowick et al. |
| 2016/0128654 A1 | 5/2016 | Wollowick et al. |
| 2016/0225192 A1* | 8/2016 | Jones ..................... G06F 3/012 |
| 2016/0277650 A1* | 9/2016 | Nagaraja .................. G06T 7/33 |

FOREIGN PATENT DOCUMENTS

| | | |
|---|---|---|
| JP | 2010088892 A | 4/2010 |
| JP | 2012-020133 | 2/2012 |
| WO | WO-2007-009263 A1 | 1/2007 |
| WO | WO-2013-175471 A1 | 11/2013 |
| WO | WO 2014-008613 A1 | 1/2014 |
| WO | WO2014-127354 | 8/2014 |
| WO | WO-2015-130848 A1 | 9/2015 |

OTHER PUBLICATIONS

International Search Report and Written Opinion for PCT/US2015/017603 dated Jun. 10, 2015.
Japanese office action and translation for Japanese Application No. 2016-570943, Examiner's Notice Date of Dec. 27, 2018, dated Jan. 1, 2019, pp. 1-13.
International Preliminary Report on Patentability for PCT/US2016/067587 dated Jun. 19, 2018.
International Search Report or PCT/US2016/067587 dated May 25, 2017.
Supplementary European Search Report for EP 17739110 dated Jun. 25, 2019.
Supplementary European Search Report for EP 16876926.3 (corresponding to PCT/US2016/067587) dated Oct. 23, 2019.
Baumgaertner et al., "The Value of the Tip-Apex Distance in Predicting Failure of Fixation of Peritrochanteric Fractures of the Hip," J. of Bone & Joint Surgery, 1995.
De Bruijn et al., Reliability of Predictors for Screw Cutout in Intertrochanteric Hip Fractures, Journal of Bone and Joint Surgery, 2012, vol. 94, pp. 1266-1272.
Matta et al., Single-incision Anterior Approach for Total Hip Arthroplasty on an Orthopaedic Table, Clin. Ortho. and Related Research, 2005, pp. 115-124, vol. 441, Lippincott W.
Liaw et al., A New Tool for Measuring Cup Orientation in Total Hip Arthroplasties from Plain Radiographs, Clin. Ortho. and Related Research, 2006, pp. 134-139, vol. 451, Lippincott Wiliams & Wilkins.
Mann et al., Radiographic Evaluation of the Wrist: What Does the Hand Surgeon Want to Know?, Radiology, 1992, pp. 15-24, vol. 184.
Branislav: Jaramaz et al., CupAlign: Computer-Assisted Postoperative Radiographic Measurement of Acetabular Components Following Total Hip Arthroplasty, Jan. 1, 2006, pp. 876 pp. 876-882, Medical Image Computing and Computer Assisted Intervention 1999, 2nd Int'l Conf., Cambridge, UK, Sep. 19-22, 1999, [Lecture Notes in Computer Science 1679], Springer, Berlin, DE (XP019036244, ISBN: 978-3-540-66503-8).
Office Action for Japanese Application No. 2019-186976 dated Dec. 1, 2020.

* cited by examiner

SYSTEMS AND METHODS FOR INTRA-OPERATIVE IMAGE ACQUISITION AND CALIBRATION

CROSS-REFERENCE TO RELATED APPLICATIONS

This application is a continuation of and claims priority to U.S. patent application Ser. No. 16/227,451, filed Dec. 20, 2018, which is a continuation of U.S. patent application Ser. No. 15/601,800 filed May 22, 2017 (now U.S. Pat. No. 10,182,871), which, in turn, claims the benefit of and priority to U.S. Provisional Application No. 62/339,926 filed May 22, 2016. This application is related to U.S. patent application Ser. No. 14/995,057 filed Jan. 13, 2016, which is a continuation-in-part application of U.S. patent application Ser. No. 14/630,300 filed Feb. 24, 2015, and claims priority to U.S. Provisional Application No. 61/944,520 filed Feb. 25, 2014, U.S. Provisional Application No. 61/948,534 filed Mar. 5, 2014, U.S. Provisional Application No. 61/980,659 filed Apr. 17, 2014, U.S. Provisional Application No. 62/016,483 filed Jun. 24, 2014, U.S. Provisional Application No. 62/051,238 filed Sep. 16, 2014, U.S. Provisional Application No. 62/080,953 filed Nov. 17, 2014, and U.S. Provisional Application No. 62/105,183 filed Jan. 19, 2015. This application is also related to U.S. patent application Ser. No. 14/974,225, filed Dec. 18, 2015 and U.S. Provisional Application No. 62/399,122 filed Sep. 23, 2016, by the present inventors. The entire contents of each of the above applications are incorporated herein by reference.

FIELD OF THE INVENTION

The invention relates to acquiring digital images of anatomical features such as bones within a patient and more particularly to accurately capturing digital images of a patient during surgery.

BACKGROUND OF THE INVENTION

Medical images from diagnostic imaging systems, such as radiographic images, fluoroscopy and ultrasound images generated by corresponding imaging systems, are often transmitted directly to other systems via a computer network, direct cable connection, or a wireless connection. Systems which receive the transmitted images include software analysis systems, such as preoperative or intraoperative analysis systems, and image storage systems such as PACS ("Picture Archiving and Communication Systems") systems.

One standard protocol used to facilitate the transmittal of medical images between disparate systems is DICOM ("Digital Imaging and Communications in Medicine"). This protocol is supported by medical imaging vendors such as GE (General Electric Corp.), Siemens and Fujitsu. Representative products from GE that support DICOM for direct image transmission include GE's fluoroscopic imaging systems, including the OEC 9900 Elite Mobile C-arm. While DICOM is a preferred data transfer protocol to transmit medical images, transfer techniques may be as simple as storing an image file and uploading it to another system.

The initial configuration and ongoing support of systems that incorporate image transmission functionality can present challenges in medical environments, including the reliance on IT (Information Technology) and engineering support to network and/or program software systems to support direct image transfer. When portable computing devices are brought into a hospital or surgery center for short-term use, such as for a specific surgery, setting up networked systems to facilitate image transmission can present an even greater challenge due to both technology and compliance protocols. Barriers to networking systems impede the use of systems that rely upon the direct transfer of medical images.

An alternative approach for medical image transfer that could address existing challenges would be immensely valuable. One such alternative approach could involve the use of a digital camera, connected to a computing device, to take a picture of an original medical image, also referred to herein as a primary image, displayed on a diagnostic image screen.

Healthcare professionals already sometimes share information informally by taking a camera image of an original medical image on a diagnostic imaging screen. However, taking a camera image in lieu of directly transferring a primary medical image is not traditionally supported in clinical systems, in significant part because of the great potential to introduce image distortion when taking a camera image of a diagnostic image.

This distortion can originate from the camera being held at an angle, rather than being perfectly aligned, relative to the diagnostic imaging screen when capturing a digital picture of the original image. The possibility of image distortion is particularly problematic when images are used to analyse biomechanics or other medical structures where size and physical relationships are important. As an example, preoperative and intraoperative images are often used in reconstructive orthopaedics to analyse biomechanics. The introduction of any image distortion could lead to faulty analysis and, subsequently, a suboptimal medical outcome.

The potential for image distortion presents an obstacle to using a digital camera in medical systems as a surrogate for direct image transmission techniques. It would therefore be desirable to develop a system and method that provides precise analysis and guidance of digital camera alignment, relative to an imaging screen, so that potential image distortion can be identified, avoided and/or removed.

BRIEF SUMMARY OF THE INVENTION

An object of the present invention is to provide guidance to enhance alignment of a camera device when taking a camera image of an imaging screen.

Another object of the present invention is to enable faster and more precise acquisition of spatially aligned images during a surgical procedure.

This invention features a system and method that aligns and calibrates a digital camera in relation to a primary image displayed on an image display medium, such as an imaging screen of a fluoroscopy imaging system, using an orientation unit such as an inertial measurement unit to generate calibration data. An image display medium may be any object adapted to display an image.

After acquiring the calibration data, the system and method utilizes the calibration data to guide the camera alignment such that the camera can capture a spatially aligned digital image of the primary image displayed on the imaging screen. In one embodiment, the system includes a device calibration module that calibrates a device using an inertial measurement unit or similar technology that can calculate the device's spatial orientation. A calibrated guidance module is capable of receiving calibration data and perceptibly rendering it, such as visually rendering real-time orientation of the digital camera relative to the at least two axes, to guide image acquisition using the camera. An image acquisition module is capable of capturing a digital camera image using guidance from the calibration display module. An image display and storage module is capable of either displaying and/or storing the camera image taken from within the image acquisition module.

The invention may be expressed as a method for capturing a spatially aligned digital image of a primary image of anatomy of a patient, by selecting a primary image suitable for at least one of intraoperative surgical guidance and preoperative surgical planning. A computing device and a digital camera are selected, and the digital camera is aligned with the primary image. The method further includes determining and recording the spatial orientation of the digital camera in at least two axes and communicating the spatial orientation to the computing device. The digital camera is then moved away from the primary image until an acceptable field of view of the primary image is achieved. A digital image of the primary image is obtained after confirming that the digital camera is acceptably aligned spatially with the primary image. The digital image is suitable for at least one of intraoperative surgical guidance and preoperative surgical planning.

This invention also features a system suitable for use with a digital camera placed in alignment with a primary image existing by itself or displayed on an imaging screen, the system including a memory, a user interface having a display capable of providing at least visual guidance to a user of the system, and an inertial measurement unit or other technology that can analyze device positioning. The system further includes a processor having an executable program that performs steps including recording the spatial orientation of the camera in at least two spatial dimensions when aligned with the primary image, and guiding camera alignment relative to the imaging screen when taking a spatially aligned picture.

In certain embodiments, the camera device's spatial orientation data is displayed by the computing device when the system is used to take a picture, allowing the system or user to adjust the device so as to minimize any alignment difference between the camera and imaging screen. The display and storage of spatial alignment data when taking a picture, compared to the data captured during camera calibration, allows the system or user to determine whether the image was acquired within a recommended or user-directed safe operating range. The system may provide the user with the option to either retake a picture using the device camera, or else to recalibrate the device and then retake the picture using recalibrated spatial guidance data.

BRIEF DESCRIPTION OF THE DRAWINGS

In what follows, preferred embodiments of the invention are explained in more detail with reference to the drawings, in which.

DETAILED DESCRIPTION OF THE INVENTION

Figure 1:
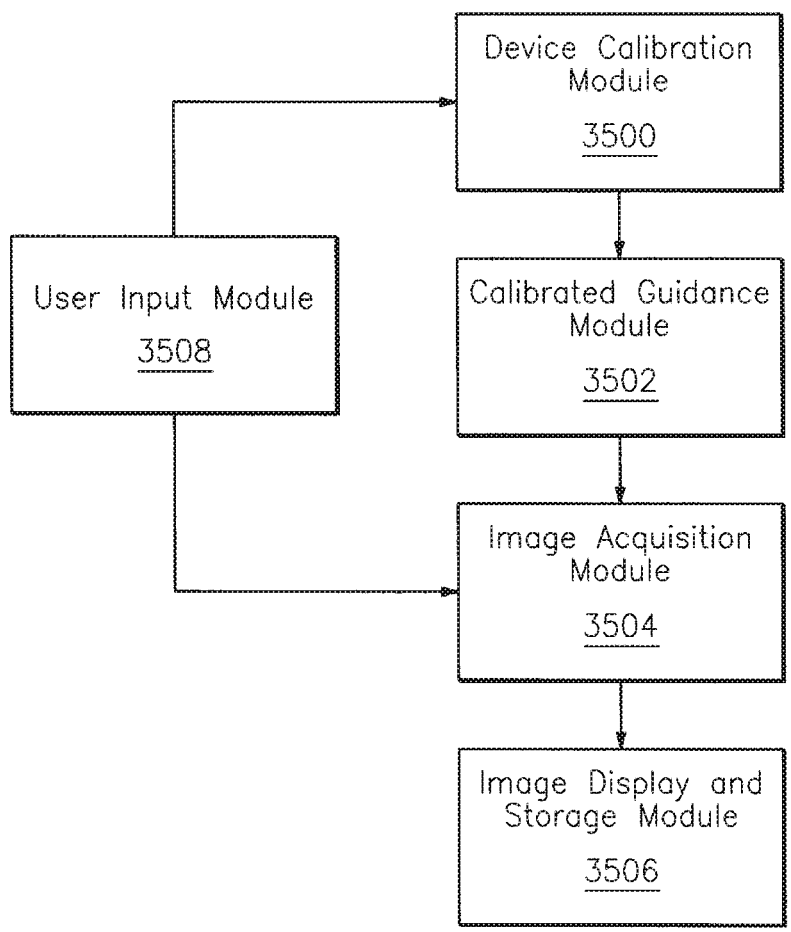
FIG. 1 is a schematic diagram of a Calibration-Guided Image Acquisition System according to the present invention.

This invention may be accomplished through a system and method that spatially aligns and calibrates a digital camera in relation to a digital monitor or similar flat surface imaging screen having a primary image, and then utilizes the calibration data to guide camera alignment when it is used to capture a spatially aligned digital picture of the primary image on the imaging screen. This is performed by spatially aligning the camera relative to the imaging screen, calibrating the camera device by recording alignment data, and then using this data to provide camera position guidance when it is used to capture a spatially aligned digital images of the primary image displayed on the imaging screen.

This system and method can be used to measure and improve the spatial alignment between a camera device and a primary image, also referred to herein as a first, reference image, such as displayed on an imaging screen; the camera is used to take a picture of the imaging screen to capture the primary image as a secondary digital image. By improving alignment, the system and method can minimize the distortion that results from taking a picture at an angle relative to an imaging screen when "taking a picture of a picture". It can also calculate any angular differences in alignment between the camera and imaging screen when the spatially aligned picture is taken.

The technology is of particular value when taking a picture of a medical image used by healthcare professionals for diagnostic purposes. Because image distortion could lead to suboptimal medical outcomes, ensuring the alignment between a camera and an imaging screen is critical if using a camera-acquired image for medical decision-making. One example of when image distortion could affect medical decisions is when using them for preoperative planning or intraoperative analysis of orthopaedics dealing with bony anatomy such as described by Wollowick et al. in U.S. patent application Ser. No. 14/630,300, also referred to as "parent application" and published as US 2015/0238271, Ser. No. 14/974,225 published as US 2016/0100909, and Ser. No. 14/995,057 published as US 2016/0128654, all incorporated herein by reference. Preoperative imaging and intraoperative fluoroscopy can be used to guide surgical decisions during hip arthroplasty, shoulder reconstruction, and spine surgery, among other orthopaedic procedures. Distortion in radiographic images could create variance or error in clinical analysis, which can lead to decision-making errors when selecting prosthetic sizes, correcting deformities, and when trying to recreate bony anatomy.

The digital camera used in this system and method is preferably an on-board camera contained within a portable computing device such as an iPad™ tablet, an Android™-enabled tablet, a Microsoft™ Tablet, a smart phone, or a similar device. Computing devices such as these generally contain an inertial measurement unit ("IMU"), which can be used in conjunction with the on-board camera to calibrate the camera alignment in relationship to the imaging screen.

Alternatively, the camera may be a separate device that communicates with a computing device. For example, the camera device may be physically separate from the computing device but connect to it directly or over a computer network. Communication between a computing device and a separate camera may be accomplished using a wireless protocol such as Bluetooth, a direct connection such as an Ethernet or USB cable, a TCP/IP internet connection, or similar technology. In cases where the camera device doesn't include an IMU, or when a computing device with an onboard camera doesn't include an IMU, alternative technologies such as digital sensors can be used to determine the spatial orientation of a device in relationship to the imaging screen, thereby providing an equivalent or "substitute" orientation system.

Broadly, techniques according to the present invention require that a digital camera device be placed in alignment with a first image, such as displayed on an imaging screen, prior to taking a picture. The system then calibrates the device by recording the spatial orientation of the camera in at least 2 of the 3 spatial dimensions when aligned with the imaging screen. Subsequently, the system uses this data to guide camera alignment relative to the imaging screen when taking a picture. This may be accomplished by various techniques that can be used to analyze the camera device position in real-time, such as by using the device's IMU or through the use of sensors. The camera device's spatial orientation data may be displayed by the computing device when the system is used to take a picture, allowing the system or user to adjust the device so as to minimize any alignment difference between the camera and imaging screen. The display and storage of spatial alignment data when taking a picture, compared to the data captured during camera calibration, allows the system or user to determine whether the image was acquired within a recommended or user-directed safe operating range. The system may provide the user with the option to either retake a picture using the device camera, or else to recalibrate the device and then retake the picture using recalibrated spatial guidance data.

In preferred constructions, software to accomplish the techniques described herein is located on a single mobile computing device that contains an on-board camera and an IMU (inertial measurement unit). In other constructions, the camera may be a separate device that interfaces with the computing device directly or over a network.

The camera device will include a spatial analysis device used to analyze the spatial orientation of the camera device relative to an imaging screen being photographed. In preferred constructions, the camera will be contained within a computing device containing an IMU, and spatial orientation will be analyzed by the IMU. IMUs in mobile computing devices generally consist of an on-board accelerometer, gyroscope, and/or magnetometer, but design variations may be used that accomplish the goal of real-time spatial tracking of the computing device. Communication of spatial data between the IMU and this application will generally be performed through the use of a software API designed to communicate IMU data to a computing device.

Figure 8:
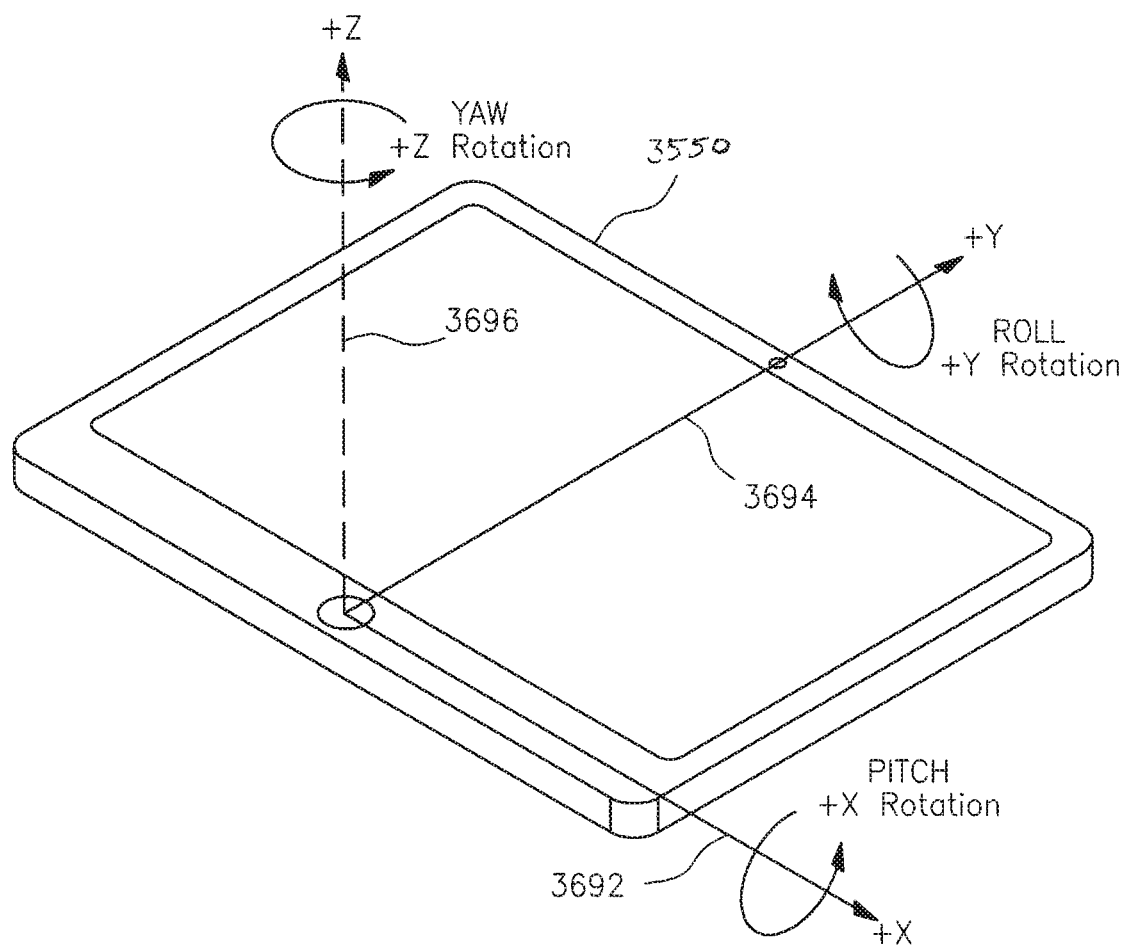
FIG. 8 is a schematic perspective view showing the device with its 3-dimensional rotation axes defined.

Mobile computing devices that contain IMUs typically track their spatial orientation and motion along 3 axes. FIG. 8 is a schematic representation illustrating these axes in relation to a computing device 3550. The x-axis 3692 and y-axis 3694 are axes that are aligned with the computing device 3550 itself. Perpendicular to the plane described by x-axis 3692 and y-axis 3694 is the z-axis 3696. Using standard spatial orientation, angular position or "attitude" nomenclature, rotation around x-axis 3692 is referred to as 'pitch', around y-axis 3694 is referred to as 'roll', and around z-axis 3696 is referred to as 'yaw'. Changing the spatial location or "linear position" of device 3550, such as linearly moving it from an off-centered position to a centered position over an image to be photographed, would involve a "translation" with additional dimensions or "degrees of freedom" that are considered in certain constructions.

In one construction utilizing an iPad, data from the IMU is shared with the system and method through the iOS operating system, which allows software applications on the iPad to use information from the IMU by subscribing to "motion events". In other words, positional changes that are recorded by the IMU are automatically sent to the iOS operating system, and subsequently software applications can be programmed to automatically receive notification from iOS when the device's position changes. This data is provided by a motion programming framework in iOS called 'CoreMotion', which is accessible by programmers developing software on the iOS platform. The data supplied is part of a software data structure called an "attitude" that contains pre-calculated Euler angle data (pitch, roll, and yaw) provided by the IMU. To spatially calibrate the iPad, a copy of data in this Attitude structure is captured at the time of calibration. Subsequent changes in Euler angles are calculated when the system analyzes device alignment by calculating the difference between updated attitude values relative to the attitudes value stored during calibration.

An alternative construction that implements this system on a Windows™ computing device will make use of a set of programming libraries available on the Windows™ operating system that are extremely similar in nature to the iOS programming libraries and related implementation details described above. Within Windows™, positional changes to the IMU may be identified using the Motion-related classes that are provided in the present Windows™ API. The Windows™ API provides the same motion "attitude" structure, including pitch, roll, and yaw, that is provided on the iOS platform, allowing spatial calibration and alignment to be implemented similarly on the Windows™ platform.

The system may alternatively track spatial orientation through the use of a stereotactic guidance component system affixed to either the camera device or imaging screen, coinciding with an independently placed control system to complete the stereotactic array. Various alternatives to track spatial orientation can also be used to calibrate and monitor spatial orientation of the camera relative to the imaging screen, such as the use of real-time sensors.

In order to analyse alignment, the system and method guides a user to calibrate a camera so that the camera device's position relative to the imaging screen can be monitored. In a preferred construction, this can be accomplished by positioning the camera device directly on the viewing screen, so that it lays flat on the viewing screen, thereby ensuring that the two devices are in a similar spatial orientation. If the camera device is contained within the computing device, the computing device itself can be positioned on the imaging viewer. If the camera is a separate device connected to the computer, the camera device can be aligned according to the imaging viewer.

Once the device is positioned to align with the imaging viewer, the system can perform calibration by registering and storing, that is, by determining and recording, its spatial alignment relative to a spatial control. In a preferred construction, the system performs its calibration using the on-board IMU within the computing device (or, if the camera device is physically disconnected, using an IMU attached to the camera device). Using the IMU, the system can record its orientation in 3-dimensional space relative to magnetic forces. In alternative constructions, the system may make use of alternative techniques to record spatial orientation described previously.

When using a computing device such as an iPad, to take a picture of an imaging screen, it is the differences in device alignment relative to the imaging screen that can create image distortion. Therefore, preferred constructions of this system will focus on analysing pitch and roll of the device relative to the imaging screen, as visually illustrated in FIG. 8. Rotation around the z-axis ('yaw') is generally not analysed, because this will merely change how the image is displayed on the screen, but not create any image distortion. However, z-axis alignment can also be displayed by particular constructions of the system if desired. Calibrating alignment relative to the z-axis is useful when the system will be used to take a picture that keeps the position of the image consistent relative to both the camera device and the imaging screen. For example, when analysing a preoperative and intraoperative image of bony anatomy in a surgical procedure, the user may wish to analyse z-axis alignment in order to align the display of both images in relation to the computing device. Maintaining image alignment could be of useful to an orthopaedic surgeon that does a visual inspection of more than one image.

After calibrating the camera, the system and method will provide spatial alignment guidance when a picture is taken of the imaging screen. Guidance provided can include real-time data determining spatial orientation along two or three axes. In preferred constructions the system will provide a recommended "safe zone", based on a maximum acceptable deviation in alignment. The range of acceptable deviation in alignment of the camera and imaging screen, known as the "Camera Safe Zone", can vary depending upon the specific use of the system and method. In preferred constructions, the acceptable range for variation will be between +/−3 to 5 degrees along any axis being analyzed. This range provides some tolerance that facilitates use of a free-standing camera, while also minimizing the potential for distortion. Anything outside of the acceptable range along an axis would cause the system to generate an on-screen warning message, or in some constructions, would prohibit the user from taking the picture. Alternatively, the system may simply provide real-time spatial data to guide alignment during image capture.

Finally, the system may allow the user to take a digital camera image to store and/or display for immediate or later use. Spatial orientation data describing the camera's orientation in space at the time of image acquisition may be stored along with the image itself. In preferred constructions, the system will allow the user to retake an image, or alternatively to recalibrate the camera device and then retake the image.

The initiation of this process is generally from within a medical software application that will use this image acquisition technique as an alternative to direct transmission of a medical image. Therefore, a system according to the present invention may function as an 'image acquisition sub-system' that is implemented within an existing medical system. For example, an existing software system may take input from a PACS system, fluoroscopic c-arm, or similar system that contains medical images using DICOM or a similar direct transfer protocol. Instead of this functionality, a user may select an option within the software to initiate the process of calibrating the device and then take a picture of the primary image on an imaging screen.

This system may be implemented by writing customized software code in any of the software languages provided within the operating system in which it is implemented. Preferably, the software language used will be a standard language for the operating system, with accessibility to the operating system's API so that measurements from the IMU (or substitute orientation-type mechanism) can be accessed directly. Examples of languages that may be used on the Windows™ Operating System include C #, Java, Python, and C++, among others. Common languages that could be used within iOS include Objective-C, Swift, and C #, among others. Languages that could be used within an Android (or LINUX-based OS) include Python, Java, and C #, among others In a preferred construction, a method according to the present invention begins in the Flowchart A in FIG. 2 with initiation of the image acquisition process, step 3520. In one construction, the process can be initiated with User Input Module 3508, FIG. 1, which enables the user to press a digital button (typically a soft key icon) on a touch screen image generated within a medical software application or "app" according to the present invention that initiates this process of calibrating the camera and taking a picture using alignment guidance. The option to initiate this process may coexist with other methods within the medical software application to upload an image, such as direct image upload using DICOM.

Figure 2:
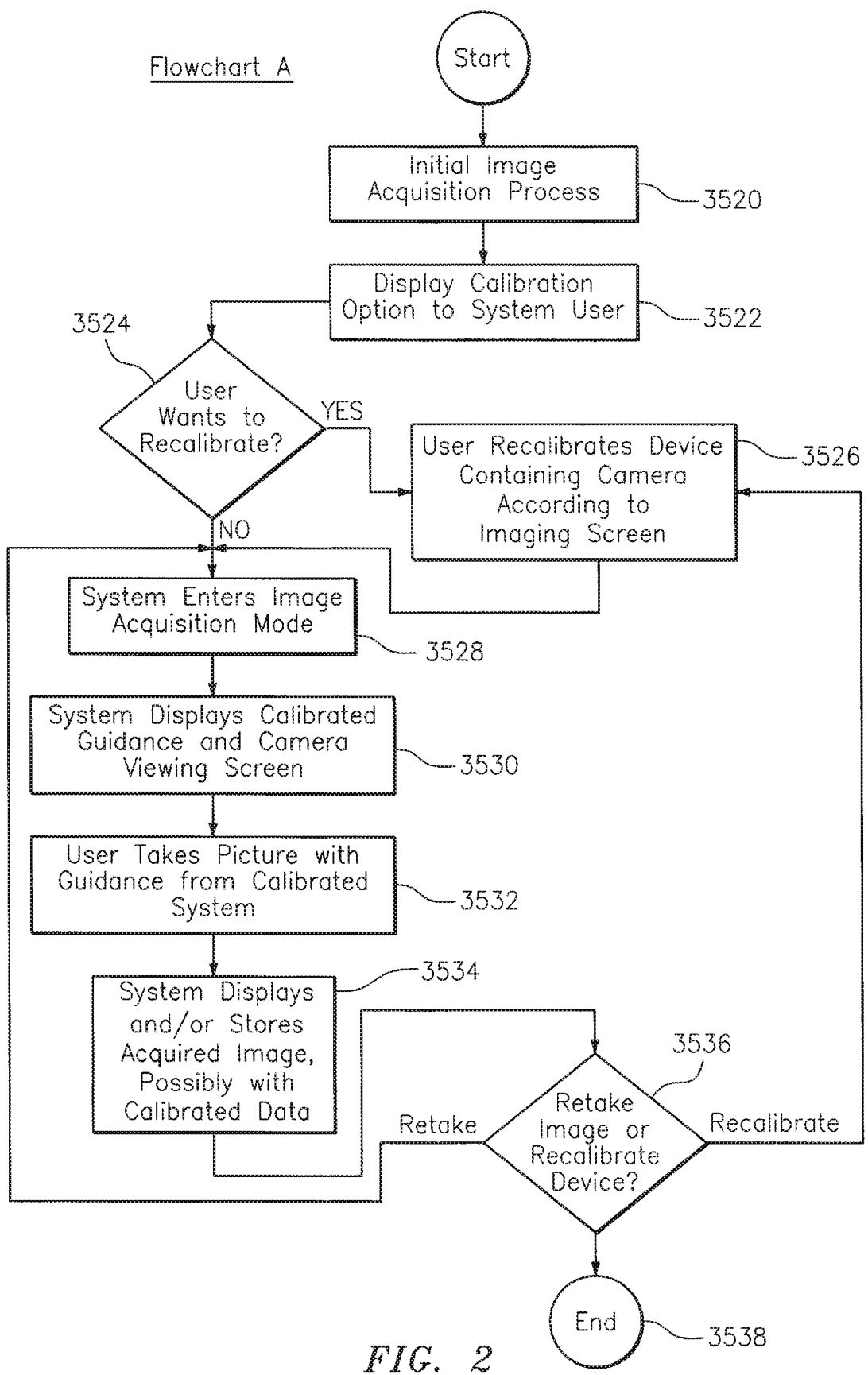
FIG. 2 is a flowchart showing the use of image calibration to provide calibration guidance for image acquisition using a camera.

After initiating the method, the Device Calibration Module 3500, FIG. 1, displays calibration options to the user in step 3522, FIG. 2. One option initiates calibration of the camera device. An alternative option allows the user to skip the process of recalibrating the camera and instead use calibration data from an earlier calibration of the device. This is appropriate when using a software application to take a picture of a stationary imaging screen multiple times. As an example, a user may take multiple pictures of the same fluoroscopic imaging screen during a hip replacement surgery for use in the analysis of biomechanics. If this system is used to take multiple pictures of the imaging screen during surgery, there would only be a need to perform an initial calibration if the fluoroscopic imaging screen were to remain stationary during surgery.

In Step 3524, FIG. 2, User Input Module 3508, FIG. 1 captures which of the calibration options presented in Step 3522 was selected. If the user indicates that they want to recalibrate the camera, the system continues with step 3526, FIG. 2. In this step, Device Calibration Module 3500, FIG. 1 guides the user in calibrating the camera device according to the imaging screen. In preferred constructions, the system will guide the user to position the camera so that it lies directly flat in relation to the imaging view screen to be photographed. For example, when the camera is located within a flat mobile computing device such as an iPad, the user will place the device so that it lays flat upon the imaging screen. The calibration module will then use the IMU to collect and record spatial calibration data.

Most constructions of this system are concerned with storing and analysing calibration data along the x and y axis as depicted in FIG. 8, because "pitch" and "roll" of the device can lead to image distortion. As described earlier, some constructions of this method will also be used to calibrate according to the z axis so that it can subsequently track 'yaw' of the device as it moves when a picture is taken. If z-axis calibration is desired, it is recommended to hold the computing device up to the side of the imaging screen, so that the sides of the device are aligned with the sides of the imaging screen. This will facilitate the process of re-calibrating the device along the z-axis if calibration is performed multiple times.

If the user wants to use data from a previous calibration to guide device alignment when taking a picture, the system can skip step 3526, FIG. 2, and continue by showing the camera alignment and camera viewing screen in step 3530, FIG. 2. This mode will be controlled by Image Acquisition Module 3504, FIG. 1 and Calibrated Guidance Module 3502, FIG. 1.

Alternative constructions may require that the device is recalibrated each and every time the user wishes to take a picture using this functionality. This could be a requirement in the case of medical applications to ensure that no error is introduced into the medical system due to incorrect use of the software. For example, the system may be implemented to require calibration to be performed every time it is used if the primary image is on a mobile fluoroscopy system that is continuously being moved. Requiring recalibration can ensure that the spatial orientation of the primary image system doesn't change between when the system is calibrated and when the image is captured. In these alternative constructions, the system would bypass the calibration options presented in steps 3522 and 3524, FIG. 2, and instead go directly from step 3520 to 3526. This modification would guide the user to re-calibrate the device to guide alignment each time that the camera is used to take a picture.

Figure 3:
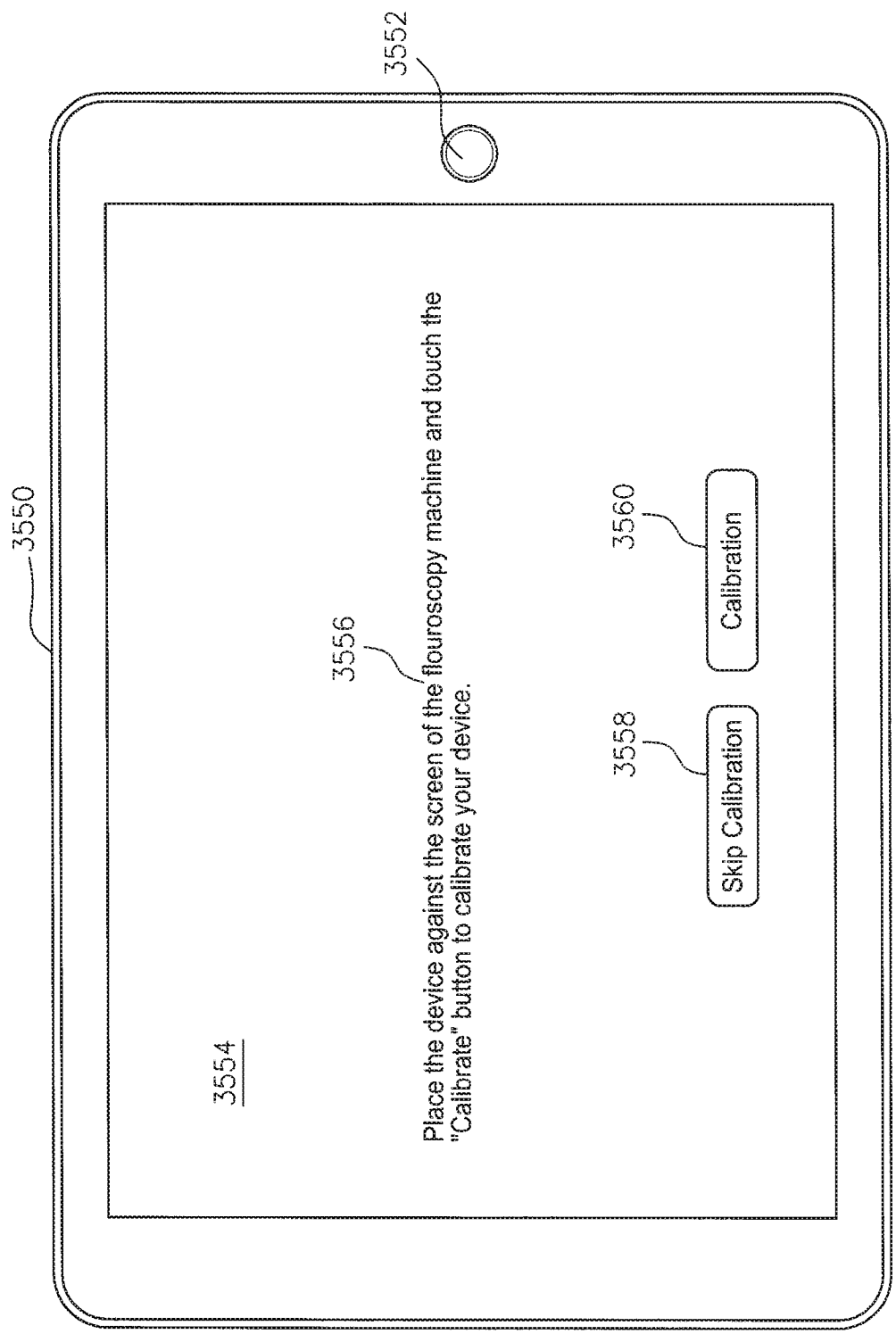
FIG. 3 is a schematic top view of a device having a display screen demonstrating how the system may guide the user to initiate the process of calibrating the device relative to an imaging viewer.

FIG. 3 is a schematic representation of a mobile computing device 3550, such as an iPad, Android tablet, or Microsoft tablet, with a digital screen view 3554, depicting the calibration options presented to the user in Step 3522, FIG. 2 by User Input Module 3508, FIG. 1. The device 3550, FIG. 3, shows a clickable device control button 3552, and the device contains an on-board digital camera that enables the device to digitally capture images. Inside of the device is an IMU, or comparable device, that generates data to the device on how the device is aligned spatially along the 3 dimensions that are illustrated in FIG. 8. On the digital screen is message 3556, guiding the user in initiating calibration of the device by laying it flat on a fluoroscopic imaging screen. Clickable buttons 3558 and 3560 provide the user with the calibration options as presented in Step 3522, FIG. 2. Button 3558 allows the user to bypass the calibration functionality and directly show the alignment guidance and camera view screen in Step 3530, FIG. 2. The user may select this option when they want to use data from a previous calibration of the device, such as when they take a picture of a stationary imaging screen to which the computing device has already been calibrated. Button 3560 directs the device to calibrate the system, as depicted in Step 3526, FIG. 2.

Figure 4:
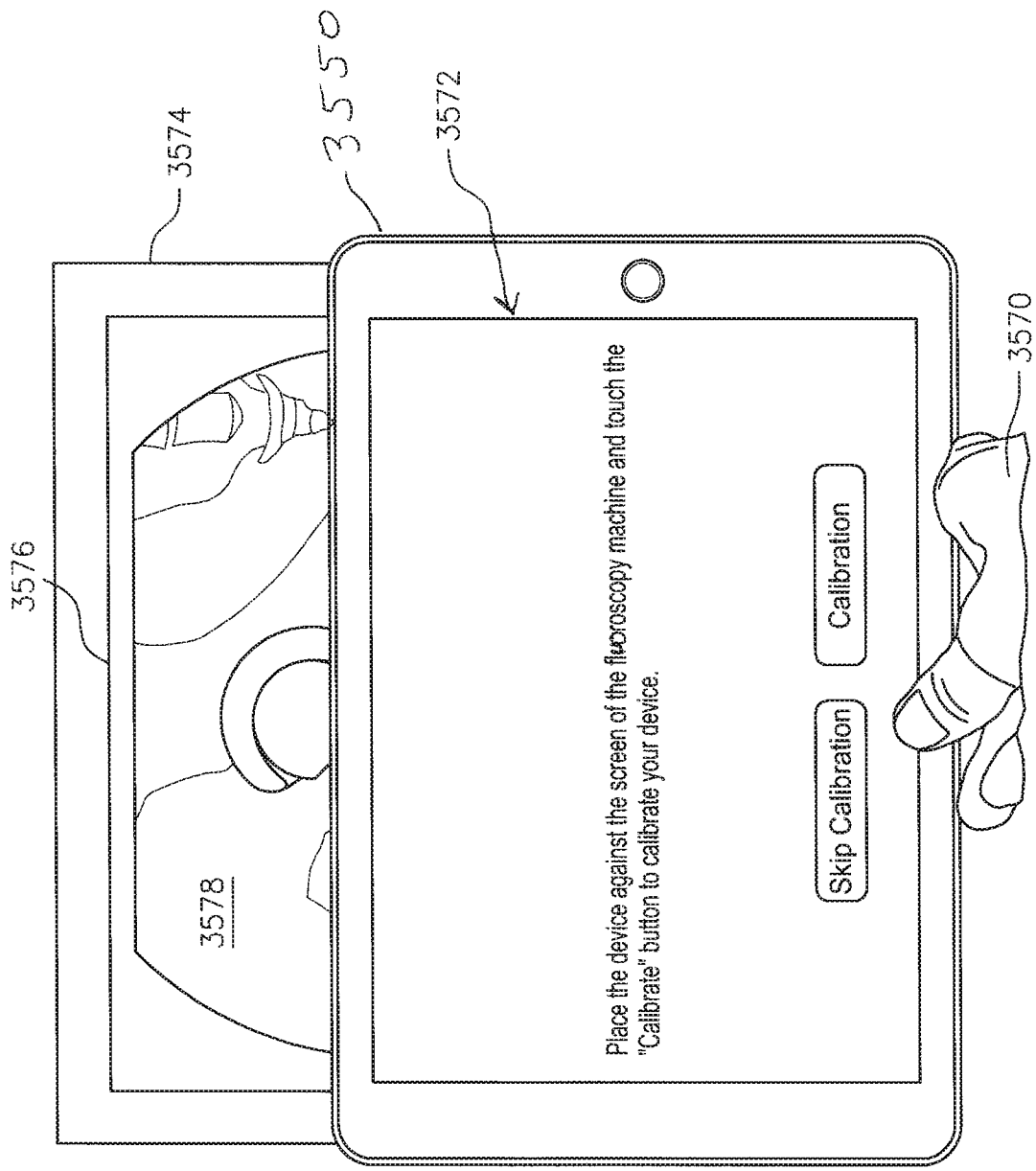
FIG. 4 is a schematic view with the device to be calibrated being placed directly on an imaging viewer.

FIG. 4 is a schematic representation of a user 3570 holding the same portable computing device 3550 as that illustrated in FIG. 3, so that it lies directly on a medical imaging monitor 3574. The computing device 3550 contains an on-board camera and is displaying screen 3572 with instructions to the user such as "Place the device against the screen of the fluoroscopy machine and touch the "Calibrate" button to calibrate your device." The monitor 3574 includes an imaging screen 3576 showing a displayed medical image 3578. To calibrate the device along the x and y axes, the user holds the computing device 3550 directly on the imaging screen 3576 or monitor 3574 so that the computing device is spatially aligned with the imaging screen. If alignment of the z-axis is also desired for a particular construction, the user 3570 should hold the computing device so that two of its borders match two of the borders of the imaging screen. For example, the computing device could be held so that the bottom and right borders of the computing device and imaging screen are on top of one another.

Figure 5:
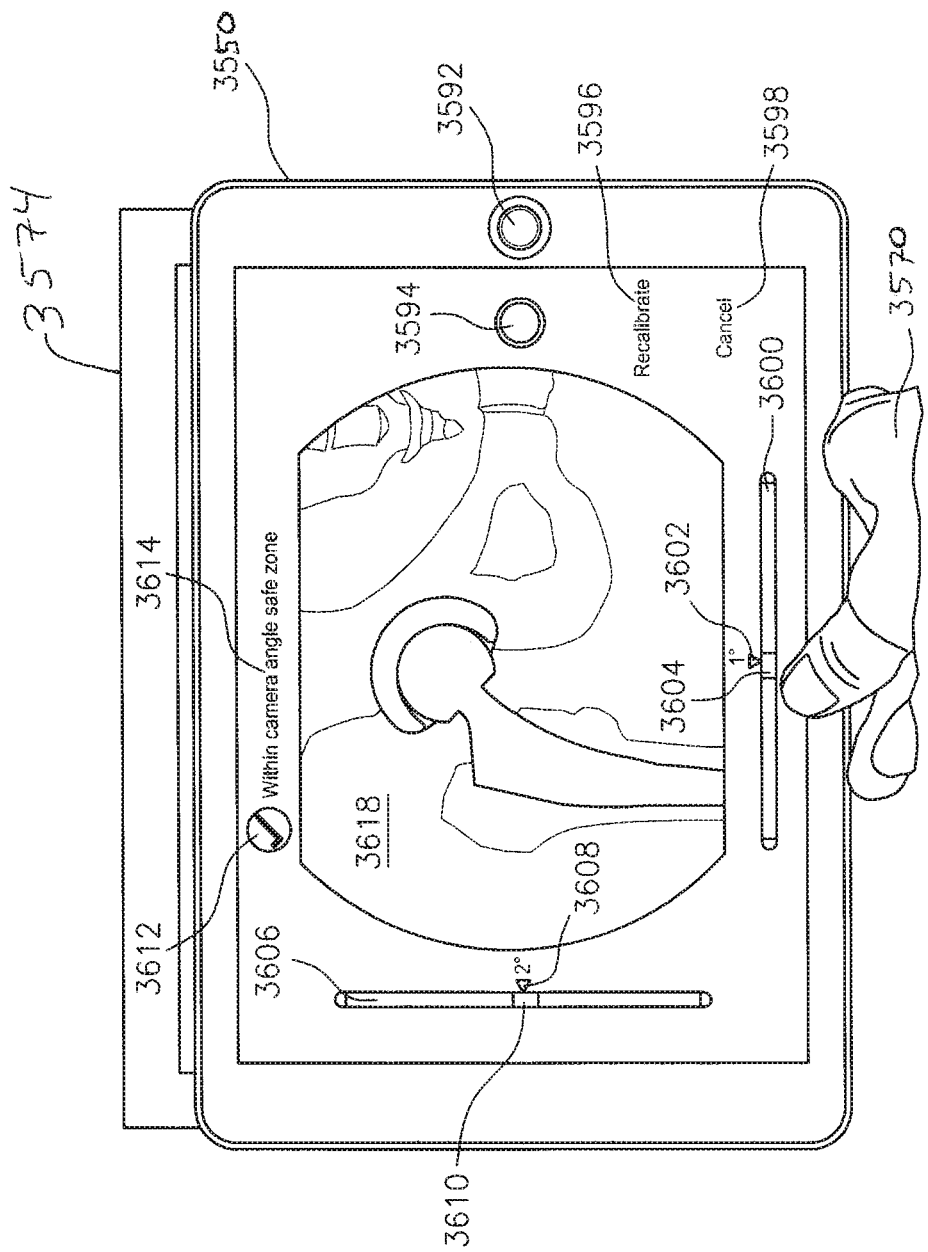
FIG. 5 is a schematic view of the device held in front of an imaging viewer to take a camera image using the calibrated device.

After the user either performs calibration of the device, selects the "Skip Calibration" button, or otherwise uses a previous calibration, the system continues in Step 3530, FIG. 2, by rendering on-screen calibrated guidance and a camera image viewing screen as illustrated in FIG. 5. In this step 3530, FIG. 2, the Image Acquisition Module 3504, FIG. 1, generates the viewing screen that shows the camera image that will be taken. This is a real-time display of the image that the camera would take, similar to the real-time camera displays shown when using a camera on an iPad or similar device. Calibrated Guidance Module 3502, FIG. 1, displays real-time data showing the real-time spatial alignment between the camera device and the imaging screen. Preferred constructions will use a computing device with an IMU to provide continuous feedback of the device orientation in relationship to the imaging screen. Preferred constructions will calculate pitch and roll, as illustrated in FIG. 8, relative to the calibrated data calculated in earlier steps. Yaw may also be calculated when there is a desire to maintain consistency in how images are displayed relative to the screen. The computing device will display some manifestation of the calculated data, allowing the user to adjust the position of the camera accordingly so that it is more precisely aligned with the imaging screen. Preferably, the system will show the calculated value in degrees of pitch, roll, and possibly yaw on the screen as the camera is positioned, and also indicate whether any of the alignment measurements are outside of a safe operating zone.

In step 3532, FIG. 2, the user takes a picture of the imaging screen using the real-time guidance provided by the computing device. Input Module 3508, FIG. 1 makes use of a digital button or similar user input feature, allowing the user to tell the computing device when to take a picture. As part of this image acquisition process, the system and/or user will analyse camera alignment data to align the camera with the imaging screen as closely as possible. Image Acquisition Module 3504, FIG. 1, completes this step by providing the mechanism to take the camera image.

FIG. 5 is a schematic representation of the user 3570 holding the portable computing device 3550, such as an iPad, in front of the fluoroscopic imaging screen 3574, but with space between the two devices 3550 and 3574 so that the user can take a camera image of the primary image seen on the fluoroscopic imaging screen 3576, that is, the digital camera of computing device 3550 achieves an acceptable field of view of the primary image. In the device screen is a viewing panel 3618 that displays the image that the digital camera views in real time. When positioned correctly, viewing panel 3618 will show the image displayed on the fluoroscopic imaging screen behind it. Calibration guidance windows 3600 and 3606 show the position of the device relative to the imaging screen on which the device has been calibrated. Pointers 3602 and 3608 display the orientation of the device, along two axes, relative to the calibration. Pointer 3602 indicates that the device is positioned 1 degree off of calibrated alignment along one axis, and object 3608 indicating that the device is 2 degrees off of calibrated alignment along the other axis. Objects or "digital bubbles" 3604 and 3610 function as levels that graphically depict the positioning of the device relative to the calibrated device, which functions as the 'neutral axis'. Check mark icon 3612 and message 3614, "Within Camera Safe Zone", are displayed in this image because the device positioning is within an established error threshold along both axes, relative to neutral positioning, as the user attempts to take a camera image with the device.

While not shown in FIG. 5, alternative constructions may show changes in yaw along a third axis by rendering a calibration level that is similar to objects 3600 and 3606, but on a 45-degree angle to indicate that it represents z-plane rotation. In yet other constructions, one or more linear translation graphics or other indicia are presented to the user.

Figure 6:
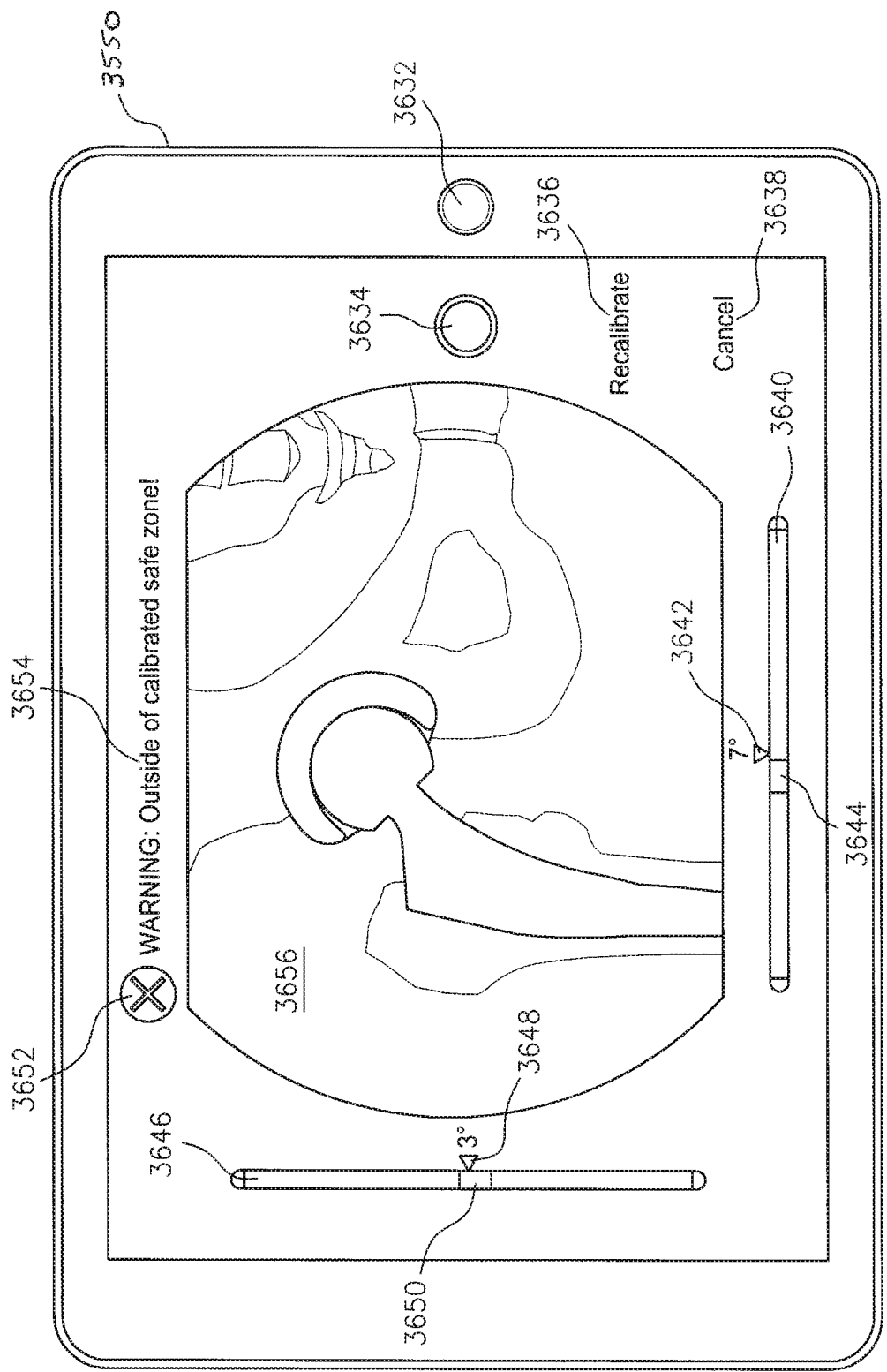
FIG. 6 is a schematic view showing the device screen display when the user holds the device outside of a "safe zone" according to the device calibration.

FIG. 6 is a schematic representation of device 3550 with navigation button 3632 again using a calibrated camera for image acquisition, depicting a schematic screen representation of when one or both axes is outside of a defined threshold of safety. In this representation, view panel 3656 depicts what is seen through the camera device, and digital button 3634 allows a user to take a picture. Clickable text object 3636 enables device recalibration, and clickable text object 3638 allows a user to cancel and exit the system. Calibration guidance windows 3640 and 3646 show the position of the device relative to the imaging screen on which the device has been calibrated. Pointers 3642 and 3648 display the orientation of the device, along two axes, relative to the calibration. Pointer 3642 indicates that the device is positioned 7 degrees off of neutral one axis, and pointer 3648 indicates that the device 3550 is positioned 3 degrees off of neutral along the other axis. Objects 3644 and 3650 function as levels that graphically depict the positioning of the device relative to the calibrated device, which functions as the 'neutral axis'. Warning icon 3652 indicates and message 3654, "WARNING: Outside of calibrated safe zone!", are displayed in this image because the device positioning is outside of an established error threshold in at least one axis, relative to neutral positioning, as the user attempts to position the device to take a camera image. In this particular image, arrow 3642 and the corresponding measurement of 7 degrees are outside of the digital box icon 3644 that shows a safe alignment change of 5 degrees at most. Along with warning icon 3652 and message 3654, this visually indicates to the user whether one of both of the axes is outside of the recommended safe zone for image acquisition angle.

After taking a picture, the Image Display and Storage Module 3506 displays and/or stores the acquired image for further use in step 3534, FIG. 2. The calibration data, indicating the spatial relationship between the camera device and the imaging screen, may additionally be output to the screen and/or stored along with the acquired image.

User Input Module 3508, FIG. 1 enables the system to determine in Step 3536, FIG. 2 whether the device should be re-calibrated or otherwise the image retaken. If the user wishes to recalibrate the system, the system continues at Step 3526, FIG. 2. The user may simply want to re-acquire the image, in which case they can retake a camera image by returning to Step 3530. If there is no need to recalibrate the system or retake an image, the process terminates.

Figure 7:
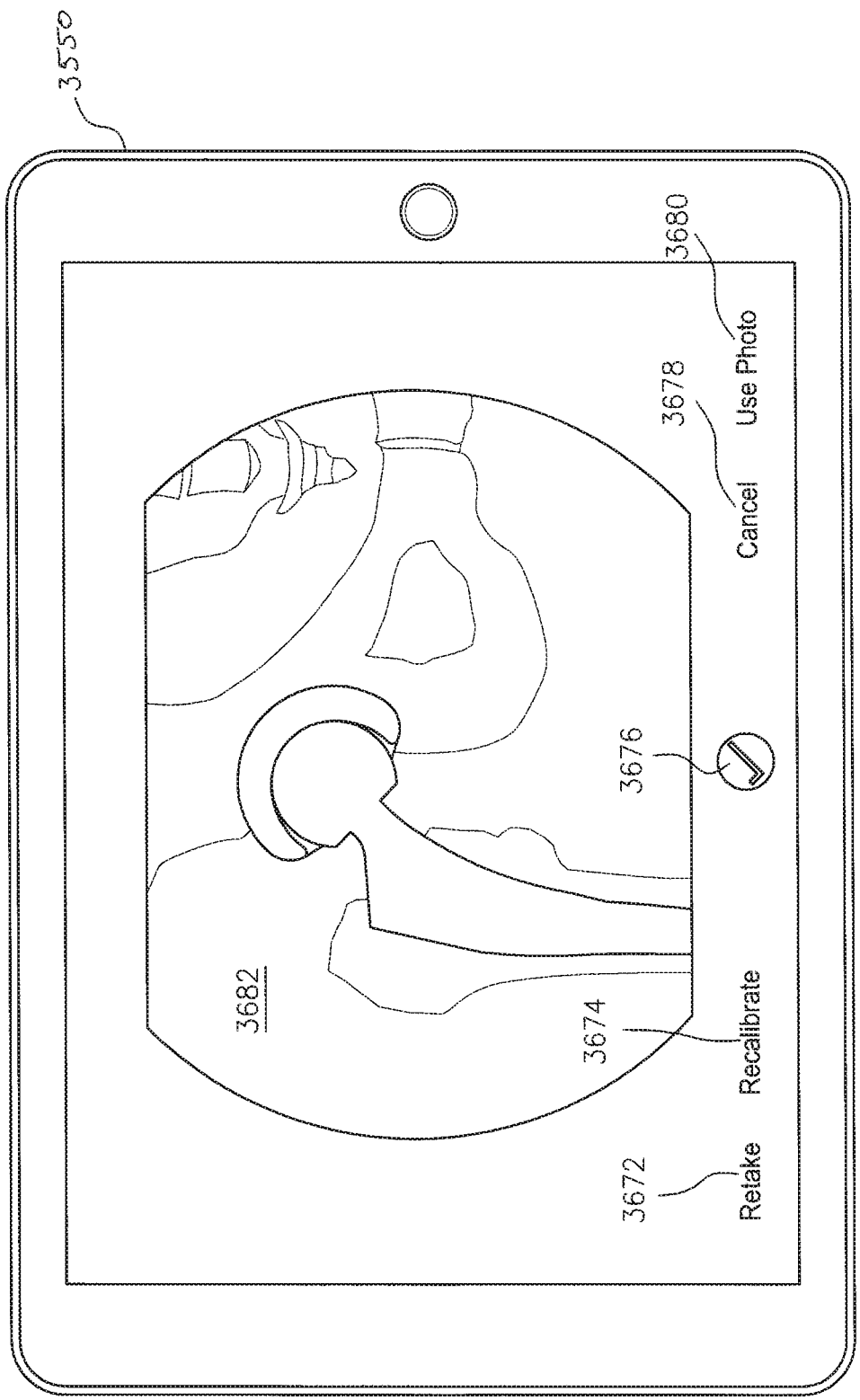
FIG. 7 is a schematic view showing the device and screen display after successfully taking a camera image.

FIG. 7 is a schematic view of the device 3550 with a schematic screen representation that displays image 3682 acquired in step 3532, FIG. 2. Check mark icon 3676, FIG. 7, indicates that the image was acquired within the safe zone based on the defined calibration. Objects 3672 and 3674 are selectable text icons that provide the navigation choices available in Step 3536, FIG. 2. Clickable text object 3672 allows the user to return to Step 3530, FIG. 2 to retake the image. Clickable text object 3674 allows the user to return to Step 3526, FIG. 2 to recalibrate the device and then retake the image. Clickable text object 3680 directs the system to use the acquired photo and finish the process. Finally, clickable text object 3678 allows the user to cancel and abort the process.

Alternative constructions will change the order of various steps, including the process of generating a calibration guide.

Although specific features of the present invention are shown in some drawings and not in others, this is for convenience only, as each feature may be combined with any or all of the other features in accordance with the invention. While there have been shown, described, and pointed out fundamental novel features of the invention as applied to one or more preferred embodiments thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated.

It is also to be understood that the drawings are not necessarily drawn to scale, but that they are merely conceptual in nature. Other embodiments will occur to those skilled in the art and are within the scope of the present disclosure.

What is claimed is:

1. A portable computing device comprising:
   a camera;
   an orientation system;
   a user interface; and
   a processor coupled to the camera, the orientation system, and the user interface, wherein the processor is configured to:
      receive, from the orientation system, a real-time spatial orientation of the camera at a current time, wherein the real-time spatial orientation of the camera is determined relative to a frame of reference in a plurality of spatial dimensions, wherein to receive the real-time spatial orientation of the camera the processor is configured to,
      receive, from the user interface at a first time prior to the current time, a camera calibration input,
      receive, from the orientation system, in response to the camera calibration input, an initial spatial orientation of the camera at the first time, and
      record the initial spatial orientation of the camera, wherein the frame of reference is based on the initial spatial orientation of the camera;
      display, using the user interface, a live camera image to be captured with the camera and an indication of the real-time spatial orientation of the camera; and
      determine, based on the real-time spatial orientation of the camera, a safe zone for image capture, wherein the safe zone is indicative of the real-time spatial orientation being within at least one established threshold relative to the frame of reference.

2. The portable computing device of claim 1, wherein the frame of reference is determined at a time of calibration of the camera.

3. The portable computing device of claim 1, wherein to determine the safe zone, the processor is configured to:
   compare the real-time spatial orientation of the camera with the at least one established threshold.

4. The portable computing device of claim 1, wherein the processor is further configured to:

initiate a capture of the live camera image in response to a determination that the camera is within the safe zone.

5. The portable computing device of claim 4, wherein the capture of the live camera image is initiated in response to user input.

6. The portable computing device of claim 4, wherein the processor is further configured to:
    initiate, subsequent to the capture of the live camera image, a calibration procedure for the camera.

7. The portable computing device of claim 4, wherein the portable computing device is communicatively coupled to a medical device; and wherein the processor is further configured to:
    initiate transmission of the captured live camera image to the medical device.

8. The portable computing device of claim 1, wherein, in response to a determination that the camera is not within the safe zone, the processor is further configured to:
    disable capture of the live camera image; or
    display an indication that the camera is not within the safe zone; or
    a combination thereof.

9. The portable computing device of claim 1, wherein the orientation system comprises:
    at least one accelerometer, or
    at least one Inertial Measurement Unit (IMU); or
    at least one gyroscope; or
    at least one magnetometer; or
    a combination thereof.

10. The portable computing device of claim 1, wherein the portable computing device is one of:
    a tablet computer; or
    a smartphone.

11. The portable computing device of claim 1, wherein the portable computing device forms part of an image acquisition subsystem of a medical device.

12. A method on a portable computing device comprising a camera, the method comprising:
    receiving a real-time spatial orientation of the camera at a current time, wherein the real-time spatial orientation of the camera is determined relative to a frame of reference in a plurality of spatial dimensions by:
        receiving, at a first time prior to the current time, a camera calibration input,
        receiving, in response to the camera calibration input, an initial spatial orientation of the camera at the first time, and
        recording the initial spatial orientation of the camera, wherein the frame of reference is based on the initial spatial orientation of the camera;
    displaying a live camera image to be captured with the camera and an indication of the real-time spatial orientation of the camera; and
    determining, based on the real-time spatial orientation of the camera, a safe zone for image capture, wherein the safe zone is indicative of the real-time spatial orientation being within at least one established threshold relative to the frame of reference.

13. The method of claim 12, wherein the frame of reference is determined at a time of calibration of the camera.

14. The method of claim 12, wherein the determining the safe zone comprises:
    comparing the real-time spatial orientation of the camera with the at least one established threshold.

15. The method of claim 12, further comprising:
    initiating a capture of the live camera image in response to a determination that the camera is within the safe zone.

16. The method of claim 15, further comprising:
    initiating, subsequent to the capture of the live camera image, a calibration procedure for the camera.

17. The method of claim 12, wherein in response to a determination that the camera is not within the safe zone, the method further comprises:
    disabling capture of the live camera image; or
    displaying an indication that the camera is not within the safe zone; or
    a combination thereof.

18. A non-transitory computer-readable medium comprising executable instructions to configure a processor on a portable computing device comprising a camera to:
    receive a real-time spatial orientation of the camera at a current time, wherein the real-time spatial orientation of the camera is determined relative to a frame of reference in a plurality of spatial dimensions, wherein to receive the real-time spatial orientation of the camera the processor is configured to,
        receive, from the user interface at a first time prior to the current time, a camera calibration input,
        receive, from the orientation system, in response to the camera calibration input, an initial spatial orientation of the camera at the first time, and
        record the initial spatial orientation of the camera, wherein the frame of reference is based on the initial spatial orientation of the camera;
    display a live camera image to be captured with the camera and an indication of the real-time spatial orientation of the camera; and
    determine, based on the real-time spatial orientation of the camera, a safe zone for image capture, wherein the safe zone is indicative of the real-time spatial orientation being within at least one established threshold relative to the frame of reference.

* * * * *